United States Patent
Cuscuna et al.

(10) Patent No.: US 11,690,593 B2
(45) Date of Patent: Jul. 4, 2023

(54) ACOUSTIC LENS FOR ULTRASONIC TRANSDUCER PROBE WITH A MANUFACTURED TEXTURED SURFACE

(71) Applicant: KONINKLIJKE PHILIPS N.V., Eindhoven (NL)

(72) Inventors: Dino Francesco Cuscuna, Reading, MA (US); Elizabeth Brunelle, Portsmouth, NH (US); Loriann Davidsen, Andover, MA (US); Martha Gail Grewe Wilson, Andover, MA (US); Jeffrey Scott Hart, Mifflin, PA (US); Harry Amon Kunkel, III, Centre Hall, PA (US); Gerred Allen Price, Mill Creek, PA (US); James William Hackenberry, Lewistown, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 735 days.

(21) Appl. No.: 16/499,359

(22) PCT Filed: Mar. 30, 2018

(86) PCT No.: PCT/EP2018/058355
§ 371 (c)(1),
(2) Date: Sep. 30, 2019

(87) PCT Pub. No.: WO2018/178369
PCT Pub. Date: Oct. 4, 2018

(65) Prior Publication Data
US 2021/0093295 A1  Apr. 1, 2021

Related U.S. Application Data
(60) Provisional application No. 62/479,657, filed on Mar. 31, 2017.

(51) Int. Cl.
*A61B 8/00* (2006.01)
*H10N 30/02* (2023.01)
(Continued)

(52) U.S. Cl.
CPC .......... *A61B 8/4281* (2013.01); *A61B 8/4444* (2013.01); *H10N 30/02* (2023.02);
(Continued)

(58) Field of Classification Search
CPC ..... A61B 8/4281; A61B 8/4444; H01L 41/23; H01L 41/33; H01L 41/35; H01L 41/053
(Continued)

(56) References Cited

U.S. PATENT DOCUMENTS 4,671,295 A * 6/1987 Abrams ................... A61B 8/06
600/463
2014/0257105 A1* 9/2014 Dausch ................ A61B 8/4281
600/458
2016/0151044 A1 6/2016 Kim et al.

FOREIGN PATENT DOCUMENTS

| JP | H07114393 A | 5/1995 | |
|---|---|---|---|
| WO | 20150117185 A1 | 8/2015 | |
| WO | WO-2019152961 A1 * | 8/2019 | ............. G01K 11/22 |

OTHER PUBLICATIONS

International Search and Written Opinion for International Application No. PCT/EP2018/058355, filed Mar. 30, 2018, 20 pages.

* cited by examiner

*Primary Examiner* — Shawki S Ismail
*Assistant Examiner* — Monica Mata

(57) ABSTRACT

An ultrasound probe has an acoustic window (10) or lens (20) through which ultrasound is transmitted and received by a transducer array (30) located behind the lens or window inside a probe enclosure. The external, patient-contacting surface (24) of the acoustic lens or window is textured. The (Continued)

texturing of the surface of the lens or window better retains gel spread over the lens or window for an ultrasound procedure, reduces reverberation artifacts, and diminishes the appearance of scratches on the lens or window.

14 Claims, 2 Drawing Sheets

(51) Int. Cl.
    *H10N 30/08*     (2023.01)
    *H10N 30/09*     (2023.01)
    *H10N 30/88*     (2023.01)

(52) U.S. Cl.
    CPC ............. *H10N 30/08* (2023.02); *H10N 30/09* (2023.02); *H10N 30/88* (2023.02)

(58) Field of Classification Search
    USPC ........................................................ 310/311
    See application file for complete search history.

ACOUSTIC LENS FOR ULTRASONIC TRANSDUCER PROBE WITH A MANUFACTURED TEXTURED SURFACE

RELATED APPLICATIONS

This application is the U.S. National Phase application under 35 U.S.C. § 371 of International Application No. PCT/EP2018/058355, filed on Mar. 30, 2018, which claims the benefit of Provisional Application Ser. No. 62/479,657, filed Mar. 31, 2017. These applications are hereby incorporated by reference herein.

This invention relates to transducer probes for medical diagnostic ultrasound systems and, in particular, to acoustic lenses for ultrasound probes having a textured outer surface.

An ultrasound probe is the hand-held instrument with which a sonographer scans a patient. The probe contains an ultrasonic transducer element or array of elements that transmit ultrasonic energy through a portion of the probe case referred to as an acoustic window or acoustic lens. Ultrasonic echo signals returning from the body of the patient pass through the acoustic window or lens and are received by the transducer elements which convert them to electrical signals. The electrical signals are coupled by a probe cable and connector to the ultrasound system used to energize the transducer and to process and display the received echo signals. The transducer array is usually constructed as an acoustic stack, including layers of acoustic matching material on the front (emitting) surface of the elements and a layer of acoustic damping material behind the elements. Many transducer stacks also include a microbeamformer integrated circuit that can be coupled to an array. The microbeamformer drives the elements with electrical signals for transmission and receives and partially beamforms received echo signals. Microbeamformers are common in two dimensional array transducer probes which must operate and control many thousands of transducer elements.

In order to form ultrasound images of high diagnostic quality it is desirable to achieve the highest possible signal-to-noise ratios for the received echo signals. To do this it is necessary to effectively acoustically couple ultrasound energy between the transducer array and the body of the patient. This is done, for example, by bonding the transducer stack to the inside of the acoustic lens, generally with an epoxy. Alternatively, the lens can be cast on the array. The acoustic lens or window must be made of a material which is highly transmissive of ultrasound. The probe is then acoustically coupled to the skin of the patient by applying a coating of acoustic gel to the face of the acoustic lens. The acoustic gel is somewhat viscous and very slippery. Moreover, the coating of gel will often adhere to the initial location of the skin contacted by the probe, and will mostly remain in that location as the probe is manipulated over the skin surface during a scanning procedure. Thus, it is frequently necessary to apply a large quantity of gel to the probe and to reapply gel frequently during the procedure. Additionally, insufficient gel on the lens surface can result in the entrapment of air bubbles, which give rise to shadowing artifacts in the image. It would thus be desirable to improve the gel retention characteristic of the acoustic lens so that less gel can be used during a procedure and less frequent reapplication of gel is needed.

In accordance with the principles of the present invention, an acoustic window or lens of an ultrasound probe has a textured external surface. The texturing provides tiny recesses or valleys in the lens surface which help retain gel in place on the lens. While conventional understanding would lead one to believe that a textured surface would give rise to deleterious artifacts in the received echo signals, it has been found that texturing can actually reduce artifacts by improving the reverberation characteristics of the lens. Furthermore, it has been found that texturing can reduce the visibility of small scratches incurred during probe use and handling. These favorable characteristics can be achieved by producing probe windows and lenses with a range of depths and densities of texturing as described below.

In the drawings:

FIG. 1 illustrates four different views of an ultrasound probe case for a two dimensional array transducer with a textured acoustic window constructed in accordance with the principles of the present invention. Accordingly.

FIG. 2 illustrates three different views of the textured acoustic window of the probe of FIG. 1.

FIG. 3 illustrates three different views of a textured acoustic window for a probe with a one dimensional array transducer constructed in accordance with the principles of the present invention.

Figure 4A:
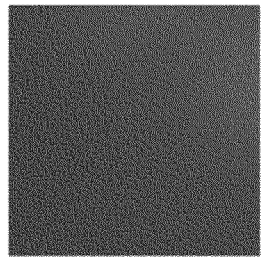
Figure 4B:
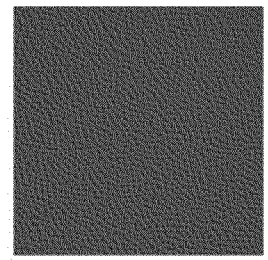
Figure 4C:
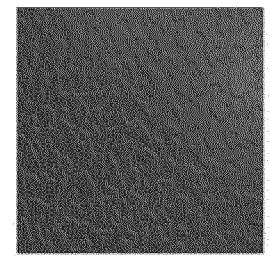

FIG. 4 shows three examples of the textured surface of an acoustic window or lens of the present invention. FIG. 4a is one example. FIG. 4b is another example. FIG. 4c is yet another example.

Figure 1A:
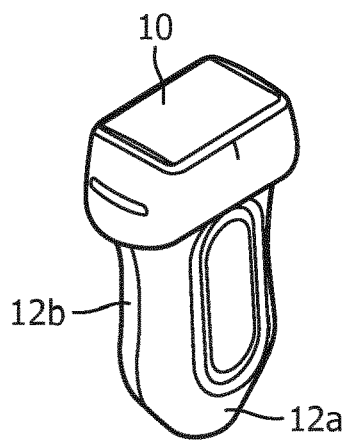
FIG. 1a is a perspective view.
Figure 1B:
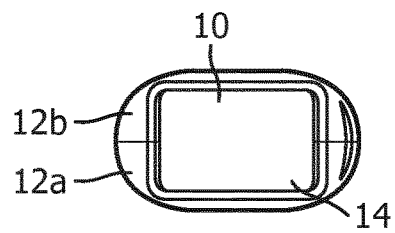
FIG. 1b is a plan view.
Figure 1C:
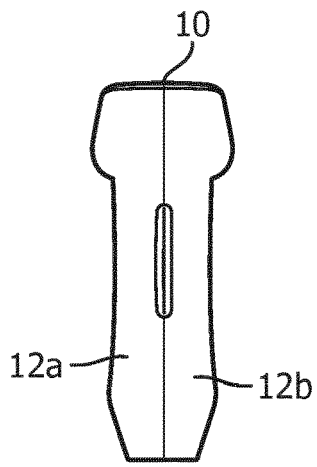
FIG. 1c is a side view.
Figure 1D:
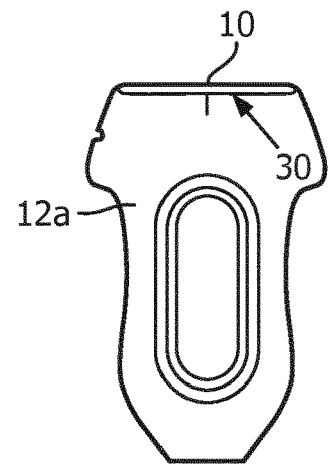
FIG. 1d is another side view of the probe case.

Referring first to FIG. 1a, a probe enclosure or case and acoustic window for an ultrasound probe of the present invention is shown in a perspective view. The probe case illustrated here is of a clam shell design with a front portion 12a and a mating back portion 12b both made of a polymeric material. Located at the distal end of the probe at the top of the drawing is an acoustic window part 10. The acoustic window part 10 is made of a molded polymer, such as an injection molded polymer, preferably a thermoplastic polyolefin, and is rectangular in shape with rounded corners. This particular acoustic window, shown in a plan view of the distal (transmitting and receiving) end of the probe in FIG. 1b, is such that the inner surface is slightly larger than the two dimensional array transducer 30 used in the probe. In a constructed implementation, the two dimensional array measures at least 6.8 cm$^2$ (17 mm by 40 mm) and preferably 8.0 cm$^2$ (20 mm by 40 mm) for excellent image quality in a variety of applications, including vascular imaging, 3D panoramic imaging, and 3D vessel cast imaging. The external surface 14 of the acoustic window is textured as described below. In this implementation the acoustic window is very slightly curved in the elevation dimension as shown in the side view of the probe case and acoustic window of FIG. 1c. The two dimensional array transducer is bonded to the inside surface of the acoustic window piece 10 as indicated by the arrow 30 in FIG. 1d.

Figure 2A:
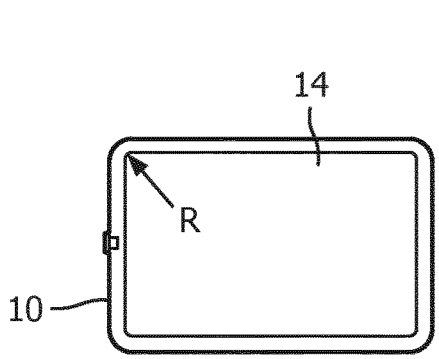
FIG. 2a is a plan view.
Figure 2B:
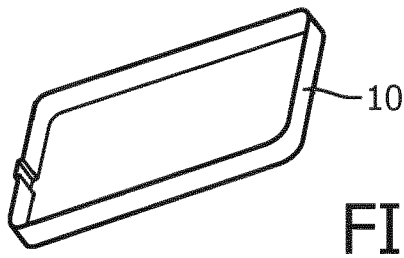
FIG. 2b is a perspective view.
Figure 2C:
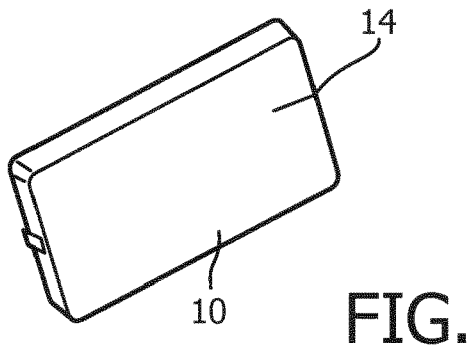
FIG. 2c is another perspective view.

The acoustic window 10 of FIG. 1 is shown in the enlarged views of FIG. 2. This particular acoustic window piece is formed with a raised lip around the sides as FIG. 2 shows. The arrow R in FIG. 2a indicates the slight rounding of the corners of the piece 10. The raised lip gives the piece a dish-like shape as best shown in FIGS. 2b and 2c, which fits inside the distal end of the probe case. The array transducer 30 is bonded to the inner surface of the acoustic window, the surface facing upward in FIG. 2b. The outer surface 14 is textured in accordance with the present invention as best shown in FIG. 2c.

Figure 3A:
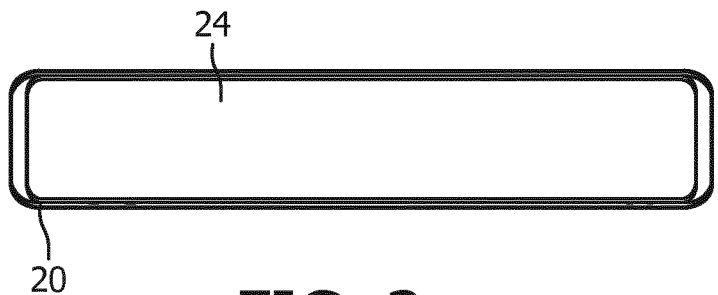
FIG. 3a is one such view.
Figure 3B:
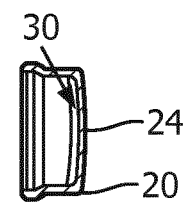
FIG. 3b is another view.
Figure 3C:
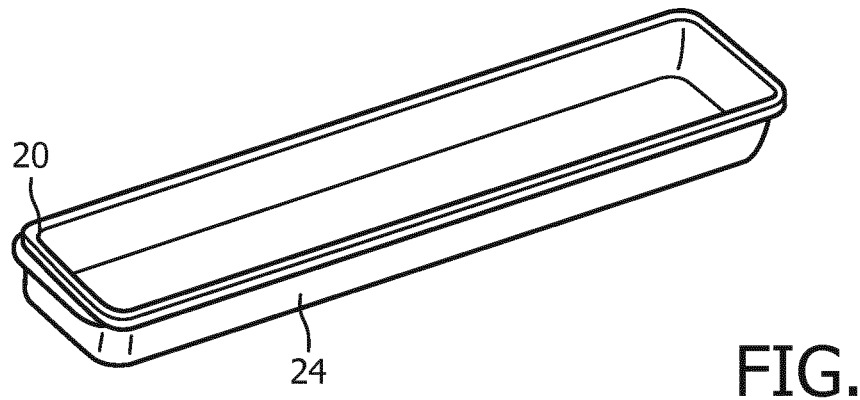
FIG. 3c is a third view.

An acoustic lens 20 for a one dimensional array transducer is shown in FIG. 3. Like the acoustic window piece 10 of FIG. 2, the acoustic lens 20 of FIG. 3 is formed of an injection molded thermoplastic olefin and has a raised lip around the sides that fits with the probe case, as best shown in FIG. 3c. The outer surface 24 of the acoustic lens 20 which faces the viewer in FIG. 3a is textured as described below. The cross-sectional view of FIG. 3b shows the acoustic lens 20 with an array transducer 30 bonded to its inner surface. The horizontal dimension of FIG. 3a is the azimuth dimension of the array transducer and the vertical dimension is the elevation dimension of the array. As FIG. 3b shows, the acoustic lens surface 24 is curved in the elevation dimension to provide focusing of the acoustic energy in the elevation dimension.

In accordance with the principles of the present invention the external surface of the acoustic window and acoustic lens of the preceding drawings is textured as illustrated in the surface images of FIG. 4. The texturing produces a surface of raised and recessed regions as these drawings illustrate. The texturing of the surface is both visible to the naked eye as FIG. 4 illustrates, and can be felt tactilely when a finger is rubbed against the surface. The pattern of the texturing can be a regular pattern or a randomized pattern as shown in these examples, with a randomized pattern being preferred. The most desirable difference in height between the most elevated points and the deepest points of the texturing can vary from one mil (0.001") to four mils (0.004"); when the texturing depth exceeds four mils, some users may sense that the texture is becoming rough to the touch. In the example of FIG. 4a the texturing has a depth of one mil, whereas the examples of FIGS. 4b and 4c show samples with 1.5 mil deep texturing. The density of the peaks and valleys of the texturing over the surface area can vary, for example, over a wide range from 5% and 95%, 10% and 90%, 20% and 80%, 30% and 70%, 40% and 60%, or 60% and 40%. That is, 20% of the surface can be recessed valleys and 80% can be projections at one extreme, and 80% of the surface can be recessed valleys and 20% can be projections at the other. In most implementations the ratio of peaks to valleys will be near 50%, such as 60%/40% or 60%/50%. The areas of the peaks can be very small, less than one mil, or much larger such as the larger, more planar raised areas which give the surface a mottled appearance as shown in the example of FIG. 4c. All of the illustrated examples have exhibited a superior ability retain gel that is spread over the surface of the window or lens, as the gel will fill the valleys of the textured surface which better retains it in place. The external surface 14 of the acoustic lens of FIG. 1b has a surface area of over 12 cm². It is difficult to retain gel over a lens area this large during use of the probe, a problem which is addressed by the texturing of the external surface of the lens. The textured surfaces have further been found to retain the gel better as the gel-covered lens is moved over the skin of a subject, as the recesses of the texture retain some gel even while the probe is moved in contact with the skin. And as mentioned above, the textured surface also has been found to exhibit better reverberation performance. When the probe is used in the vicinity of strong reflectors, such as the ribs when doing cardiac scanning, ultrasound waves reflected back from the ribs can be reflected from a smooth lens surface back into the subject, causing unwanted reverberation echoes. The textured surface will provide some scattering to these back-reflected waves, reflecting more discontinuous wavefronts that cause reduced reverberation artifacts in an image. The visibility of scratches on the lens arising during normal probe handling and use is also markedly diminished with the textured lens surface.

While the texturing can be formed on the surface of a previously produced smooth lens, the preferred technique is to form the textured surface during injection molding of the lens or window. The surface of the mold which forms the external surface of the lens or window is impressed, embossed, etched, or otherwise constructed to have a reverse of the textured surface so that the injection molding of the lens or window will produce the finished piece with the desired textured surface. Alternatively, texturing can be produced using a cast material, such as RTV or polyurethane.

It should be noted that the limitations of the following claims are not written in means-plus-function format and are not intended to be interpreted based on 35 U.S.C. 112, sixth paragraph, unless and until such claim limitations expressly use the phrase "means for" followed by a statement of function devoid of further structure.

What is claimed is:

1. An ultrasound probe for imaging internal anatomy of a patient comprising:
a probe enclosure;
a transducer array located in the probe enclosure;
an acoustic lens formed of a molded polymer, forming a part of the probe enclosure between the transducer array and an exterior of the probe enclosure, the acoustic lens having a manufactured textured external surface; and
a coating of acoustic gel located on the manufactured textured external surface and retained on the manufactured textured external surface by filling recesses or valleys of the manufactured textured external surface,
wherein the acoustic lens and the coating of acoustic gel are adapted to acoustically couple ultrasound energy into the internal anatomy of the patient, and
wherein the manufactured textured external surface is adapted to scatter ultrasound waves reflected back to the ultrasound probe from ribs in the internal anatomy of the patient to thereby reduce reverberation artifacts in an image.

2. The ultrasound probe of claim 1, wherein the molded polymer further comprises a thermoplastic polyolefin.

3. The ultrasound probe of claim 1, wherein the manufactured textured external surface further exhibits a regular pattern.

4. The ultrasound probe of claim 3, wherein the manufactured textured external surface further exhibits a randomized pattern.

5. The ultrasound probe of claim 1, wherein the manufactured textured external surface further comprises a plurality of peaks and valleys.

6. The ultrasound probe of claim 5, wherein a difference between a height of the plurality of peaks and valleys is within a range of one to four mils (0.001" to 0.004").

7. The ultrasound probe of claim 6, wherein a difference between a height of the plurality of peaks and valleys is approximately 1.5 mils (0.015").

8. The ultrasound probe of claim 5, wherein a ratio of the peaks to the valleys of the manufactured textured external surface is within a range of 20% to 80%.

9. The ultrasound probe of claim 8, wherein the ratio of the peaks to the valleys of the manufactured textured external surface is within a range of 40% to 60%.

10. The ultrasound probe of claim 1, wherein the transducer array further comprises a one dimensional transducer array.

11. The ultrasound probe of claim 1, wherein the transducer array further comprises a two dimensional transducer array.

12. The ultrasound probe of claim 11, wherein the transducer array has an area of at least 6.8 cm$^2$.

13. The ultrasound probe of claim 12, wherein the transducer array has an area of at least 8.0 cm$^2$.

14. The ultrasound probe of claim 1, wherein texturing of the manufactured textured external surface is both visible and has a tactility that can be felt.

\* \* \* \* \*